United States Patent
Betts-Lacroix et al.

(10) Patent No.: US 9,700,257 B1
(45) Date of Patent: Jul. 11, 2017

(54) METHOD OF MEASURING GUT TRANSIT TIME IN ANIMALS

(71) Applicant: Vium, Inc., San Mateo, CA (US)

(72) Inventors: Jonathan Betts-Lacroix, Belmont, CA (US); Laura Schaevitz, Los Gatos, CA (US); Daniel J. Ford, San Francisco, CA (US)

(73) Assignee: Vium, Inc, San Mateo, CA (US)

( * ) Notice: Subject to any disclaimer, the term of this patent is extended or adjusted under 35 U.S.C. 154(b) by 0 days.

(21) Appl. No.: 15/363,967

(22) Filed: Nov. 29, 2016

(51) Int. Cl.
| | |
|---|---|
| *A61B 5/00* | (2006.01) |
| *A01K 29/00* | (2006.01) |
| *A01K 1/03* | (2006.01) |
| *G01N 21/64* | (2006.01) |

(52) U.S. Cl.
CPC ............... *A61B 5/42* (2013.01); *A01K 1/031* (2013.01); *A01K 29/005* (2013.01); *G01N 21/6428* (2013.01); *A61B 2503/40* (2013.01); *G01N 2021/6439* (2013.01)

(58) Field of Classification Search
CPC ........ A01K 1/031; A01K 29/005; A61B 5/42; G01N 2021/6439; G01N 21/6428
See application file for complete search history.

(56) References Cited

U.S. PATENT DOCUMENTS

| | | | | |
|---|---|---|---|---|
| 2004/0245477 A1* | 12/2004 | Matsuda | ............... | A01K 29/005 250/458.1 |
| 2009/0232949 A1* | 9/2009 | Stark | ...................... | G01N 33/02 426/231 |
| 2013/0216586 A1* | 8/2013 | LeBrun | ................ | A61K 31/716 424/278.1 |
| 2016/0069743 A1* | 3/2016 | McQuilkin | ........... | G01J 3/2803 356/416 |

OTHER PUBLICATIONS

Marona, H.R.N. & Lucchesi, M.B.B; Protocol to refine intestinal motility test in mice; Laboritory Animals Ltd., (2004) 38, 257-260.

* cited by examiner

*Primary Examiner* — Mark R Gaworecki
(74) *Attorney, Agent, or Firm* — Kim Rubin, Patent Agent

(57) ABSTRACT

Methods of measuring gut transit time in animals are presented. Steps include fasting an animal, then feeding it a food containing a fluorescent dye, and then monitoring bedding for fluorescent droppings by using an ultraviolet (UV) fluorescent excitation light that is in the visible range of the animal, and thus is perceived by the animal as daylight, while turning off human-visible white light so that a camera may record UV emissions without faint emission light being burned out by human-visible light. Such methods are fully automatic with continual monitoring in the home-cage of the animal. Animals may be multi-housed with automated animal-ID. A single camera may be used to observe fluorescent emission light, animal activity under white light, and animal activity under infrared (IR) light. The method may be repeated to create a measurement sequence to determine matching to a disease model.

21 Claims, 2 Drawing Sheets

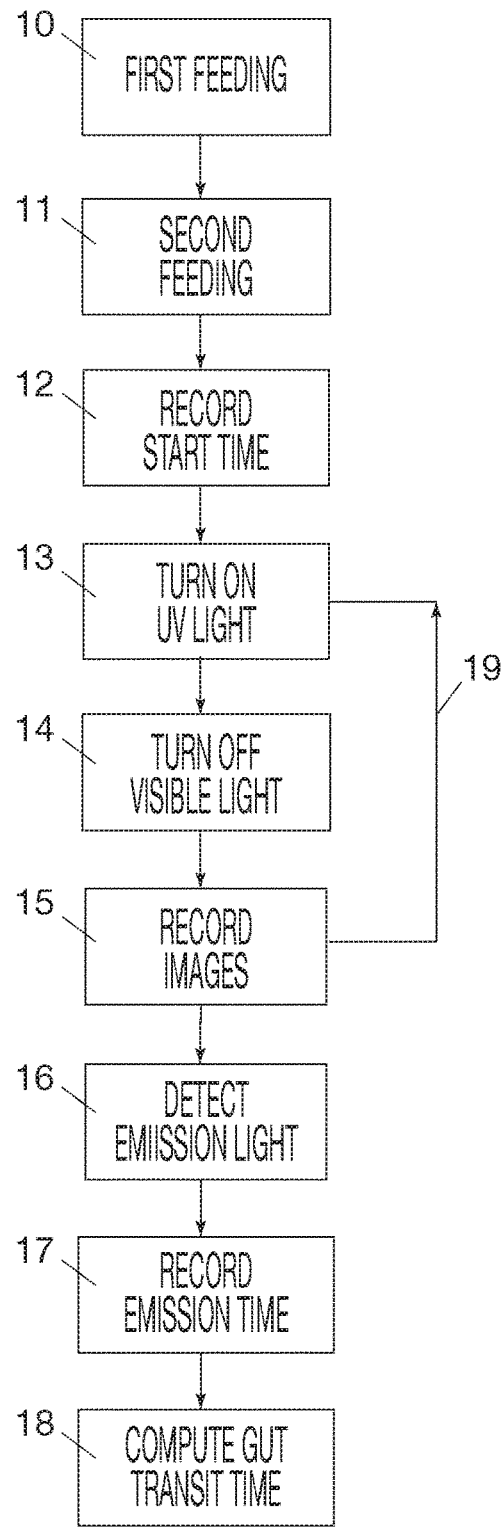

METHOD OF MEASURING GUT TRANSIT TIME IN ANIMALS

BACKGROUND OF THE INVENTION

Prior art methods of measuring gut transit time typically involve feeding an animal charcoal via oral gavage, and then either placing the animal in a specially configured cage and manually observing the animal, or killing the animal.

Gut transit time is also known as intestinal motility. Weaknesses of prior art include the time consuming and invasive practice of oral gavage, the expensive, time consuming and error-prone manual observation step, stressing an animal by placement in an unfamiliar cage, and poor time resolution and poor time accuracy of manual observations. Another weakness is the inability to take a sequence of measurements over days to track changes in gut transit time. Another weakness is the inability to multi-house animals. Yet another weakness is the practical limitation of starting the time interval during the animal's normally active, nocturnal time. Some prior art has the weakness of killing the animal.

SUMMARY OF THE INVENTION

Embodiments of this invention overcome all of the above stated weaknesses of prior art.

One exemplary embodiment of this invention first makes an animal hungry, then feeds the animal food with a non-toxic, fluorescent dye. The animal's cage is then monitored continually with a camera to observe fluorescence in the bedding. The time difference between the special feeding and the automated observation is the gut transit time.

Key embodiments do not stress the animal, such a putting it in an unfamiliar cage; removing it from its cage-mates; giving it unfamiliar or no bedding; changing light from its normal day/night timing; and handling the animal. These are major benefits in providing more accurate, realistic, useful, detailed and applicable study results.

To observed most fluorescence, typically an ultraviolet (UV) light source is used in the excitation band of the fluorescent chemical. Most non-toxic dyes fluoresce in the (human) visible spectrum. Therefore a conventional black/white or color visible light camera may be used to monitor the bedding.

However, UV light in the range of 395 nm, while idea for exciting fluorescent dyes, is also a peak wavelength in the visible light for mice. Thus, brightly illuminating a cage with this band of light is the equivalent of bright daytime light for the mouse. It is highly disruptive to mice in a vivarium study to turn on bright lights at their nighttime, when they are normally active. Therefore, the UV light should be turned only during their daytime.

To avoid turning "daytime" lights on and off, which is disruptive to the animal, normal, white, "daylight" light should be turned off synchronized to the turning on of the UV light.

Because the bedding should be inspected only during the animal's daytime, it is necessary to compute an appropriate time for the special feeding. This is computed by considering the most likely minimum and maximum gut transit times, and selecting a feeding time such that this time window after feeding will entirely fit within the animal's daytime.

So that only camera may be used for both normal, "white" light illumination, one embodiment replaces a common, mechanically activated, infrared (IR) filter with a band pass filter selected for this purpose: the band pass filter blocks the UV excitation light and passes emission light color.

It is often desirable to have multiple mice in one cage, "multi housed." One embodiment feeds the fluorescent treated food to only one animal of interest. This requires automatic detection of proper animal ID. It also requires that food course be controlled so that only the desired animal is fed the treated food.

Some embodiments take regular gut transit time measurements, such as daily. These sequential measurements are then tracked to determine how an animal's health is improving or declining. By comparing the changes in gut transit time of the animal to known disease models, it is possible to compute the most likely progress of a disease or treatment.

BRIEF DESCRIPTION OF THE DRAWINGS

FIG. 3 shows a block diagram of one exemplary embodiment.

DETAILED DESCRIPTION OF THE INVENTION

Figure 1:
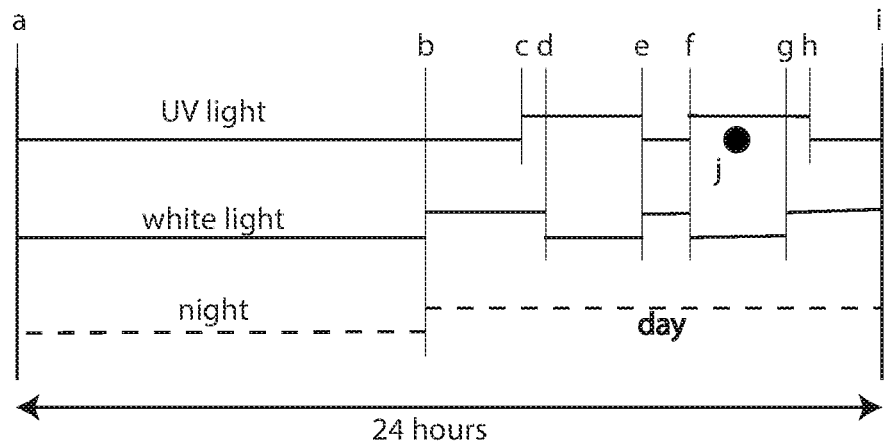
FIG. 1 shows an embodiment for timing of feeding and observing.

Descriptions below are exemplary embodiments Plain English is used for clarity, not to indicate or suggest any limitations. That is, these are typical scenarios of embodiments of methods, devices, systems or use.

Turning first to FIG. 3, we see basic embodiments. Step 10 shows a first feeding of an animal in a cage in a vivarium, for example. This first feeding may be a specific point in time, or it may be a time period. The time of the first feeding is not necessarily recorded. A key embodiment of this first feeding is that comprises no feeding at all. The purpose of providing no feeding, prior to step 11, is to make the animal hungry so that it eats the food in the second feeding of step 11. One embodiment is that step 10 is in fact a hunger period leading up to step 11. One embodiment may create hunger by simply spacing steps 10 and 11 so that this time period is the hunger period. Typically, water is provided. However, feedings of steps 10 or 11 may include any combination of food, liquid or water. Hunger may include depriving an animal of water.

Step 11 is a key starting time for measuring gut transit time. The food (or liquid) in step 11 comprises a fluorescent material, such as a dye, hopefully a non-toxic dye. This dye, at least in part, need to pass through the animals gut without losing its fluorescent property. Embodiments use fluorescent materials other than dye, such as beads, high-molecular weight molecules, edible fiber, and many other possible materials.

Steps 10 and 11 may be controlled by manual devices or automatic devices. Note that these feedings may be specifically set at times controlled by a human, or by an automatic control system, or may be primarily determined by the animal which eats when it is hungry.

In step 12 the start time of the gut measurement method is recorded. This is nominally the time of second feeding. However, with an automatic control system step 12 might occur prior to step 11. In a real-time observational system, step 12 occurs with or immediately after step 11. However, there is minimal reason to record the start time in step 12 at the same time as the feeding. For example, recorded video of the animal activity may permit much later determination of the start time. Alternatively, the feeding device could have sensors to determine the time step 11 occurs.

Important embodiments control or record which animal in a multi-housed cage (more than one animal in the same cage) is being fed in step 11. Multi-housing is also called multi-homing. This might occur by recording which animal ate the food in step 11. It might include only enabling the food of step 11 to be available when a desired animal is at a feeding station. In some embodiments more than one animal may be fed at step 11 at approximately the same time. For example, if two animals are in a cage and they are both hungry, they may both eat the second food within minutes of each other.

In another important embodiment, in a multi-housed cage, different animals are fed different food. For example, one animal may be fed dye that emits red light while a second animal is fed food that emits blue light.

Important embodiments in a multi-housed cage include automatic identification of animals are feeding at step 11. Such identification may use video and animal tail tags visible in the video, with automatic identification of the animals through video processing of images taken in the cage while an animal is feeding at step 12. In one embodiment, the camera that performs video recording to identify an animal is the same camera used to record images in step 15.

Embodiments have step 11 occur during the nighttime of the animal.

Some embodiments do not use natural feedings, such as steps 10 and 11 shown in FIG. 3. For example oral gavage may replace step 11, in which case step 10 is optional.

Another embodiment uses injections in place of step 11, in which case step 10 is optional. Any injections must use a fluorescent material will pass from the blood into the gut. In such embodiments, mucosal injury is detectable as this is the route for the fluorescent material to pass from the vascular system into the blood. Embodiments of this invention are methods to detect, measure, track and predict mucosal injury and all diseases and treatments associated with mucosal injury.

Yet another embodiment places a fluorescent material on the skin of the animal, where the material may pass into the skin to enter the bloodstream, and from there potentially to the gut, as described above with respect to mucosal injury. Any such fluorescent material placed on the skin may be mixed with or accompanied by a penetration agent such as DMSO or other known skin penetration enhancing agents. Step 10 may or may not be used. Its use may be helpful in providing a known starting gut fullness at step 11, even if step 11 is not food.

In step 13, an ultraviolet light (UV) is turned on, illuminating at least some of the litter or bedding in the cage of the animal. Bedding may be bedding material. The spectrum (also called band) of this UV light overlaps the excitation band of the fluorescent dye or other fluorescent material fed to the animal in step 11.

Embodiments have step 13 occur only during the daytime of the animal.

Some animal eyes, particularly rodent eyes, particularly mouse eyes, are very sensitive to near UV light, such as around 395 nm. Thus, turning on such light in a mouse cage appears to the mouse as daylight. It is undesirable in an animal study, such as in a vivarium, to interfere with the normal circadian rhythm of a mouse, or to turn on light at night or create artificial darkness at daytime. Thus, a UV light visible by a mouse should not be turned on during the nocturnal period of the mouse. Key embodiments avoid doing this.

UV light may be near UV, mid UV, or deep UV, as the terms are used in the art. UV light may be continuous or pulsed. Pulsed UV light is still within the meaning of "on" in step 13.

The UV light of step 13 may be turned on during the daytime period of the mouse, left on, cycled, or turned on and off for any time periods, such variations all being embodiments. One such exemplary cycling is shown in FIG. 1.

The purpose of the UV light is to excite the fluorescent material consumed by the animal in step 11, now in the bedding.

In step 14, visible light is turned off. By "visible," in this step, we mean roughly "normal daylight" that is visible to both humans and animals. It is important to distinguish, through the entirety of the specification, claims, drawings, prior art, and other prosecution material the distinction between "human visible" and "animal visible" light, as such distinctions go to the nexus of embodiments. Context for the construction of the word, "visible," is thus critical at all times.

Mice have peak vision sensitivity in two light bands, that people generally call "blue-green" and "near-UV." The purpose of steps 13 and 14 is to maintain the sense of "daytime" for the animals; while enabling a visible light camera to now record fluorescent emission light. In this way, animals in the cage are not disturbed from their normal routine, stress on the animal is reduced, and thus results as part of a study may be more accurate, consistent, detailed, or applicable.

Turning on in step 13 may include leaving on. The UV light may be left on for all or a portion of the animal's daytime. Turning off in step 14 may be changing state or leaving off, particularly if a sequence of images are taken by repeating steps 13 through 15, as shown by arrow 19, or if it is desired that all of the daytime light for the animal is provided by the UV light.

In step 15 image of the animal bedding are recorded. A camera may be a still, video, 3D, VR, or other camera. It may operate continuously, continually, in bursts, or on remote command. As discussed elsewhere herein, images may be monochrome, color, filtered, processed, or other otherwise have a number of pre-recording, during recording, or after recording actions.

In steps 15 and 16, emission light from excrement of the animal, due to the fluorescent material consumed by the animal in the second food, as excited by the UV light of step 13. In some embodiments the turning on of the UV light in step 13, including possibly pulsing of the light in step 13, may be synchronized with the recording in steps 15. For example, for a video or still camera, every other frame may have UV turned on. Then, the every other frame images may be organized into two sequences, one with UV on and one with UV off. In an alternative embodiment, the adjacent (or proximal) frames may be compared, such as subtracted, to obtain small differences in light, so as to detect faint emission light from the fluorescence.

Steps 15 and 16 may be merged into a single step or may overlap.

Step 16 may occur after or considerably after step 15. For example, video could be recorded in step 16, and then processed later in step 16. Step 16 may be performed in the cameras; in electronics associated with the camera; by a remote processor, dedicated or general purpose; in a third party system such as cloud-based computers programmed for such function; or any combination of these. Step 16 also includes "no detection." For example, a study may end or an animal may be removed from a study for various reasons (e.g., death). Nonetheless, having detected no emission light in step 16 as of a certain time may be useful information. As another example, an animal may have a blocked gut, and thus not generate fluorescent excrement. This may be the detected in step 16 by not detecting emission light. Detection in step 16 may be binary information.

Step 17 records the emission time. This time may be determined and recorded anywhere from steps 13 through to step 18. For example, time stamps, advanced planning or other time information may be used to determine when the images recorded in 15 associate with the detection in step 16. Thus determining the emission time in step 17 may be significantly decoupled from the detection in step 16. The time recorded in step 17 may be a specific time, such as 2:00 pm (and date), or a time window, such as between 2:00 pm and 2:05 pm, or a limit, such as after 3:00 pm or before 6:00 pm. The time in step 17 may be for more than one animal, as discussed elsewhere herein. The time in step 17 may be a statistical function, such as a mean, mean and standard deviation, or any statistical distribution function, including probability models and functions.

Embodiments include recording cage location where the emission light was detected instep 16.

Embodiments include recording the number of locations where emission light was detected in step 16.

Embodiments include recording animal ID associated with the emission light in step 16.

Embodiments include recording other animal activity before, during or after excrement, such as sleeping, eating, exercising, sex, fighting, and the like.

Embodiments specifically include using the same camera as used in step 15 to record the activities or animal ID in the above embodiments.

Step 18 computes gut transit time by nominally subtracting the start time from the emission detection time. Note that since either or both the start and end times may be time windows, have statistical distributions, or probability distributions, "subtraction" includes the necessary arithmetic and statistical steps to properly compute the resulting difference.

Step 19 reflects the reality that one most useful way to use embodiments of this invention is to monitor a cage on a regular basis, such as continuously, continually, in bursts, or on some other basis, looking of fluorescent animal excrement. One might record 30-frame per second video, for example, for an entire daytime period of eight hours. It may be more efficient, however to record a single frame every 2 minutes (or 1, 5, 10, 15, etc.). It may be advantageous to record 5 to 60 seconds of video in a burst. One reason is that the animal may be covering fluorescent excrement, at a given moment in time. Another reason is that it may be advantageous to average multiple video frames, such as to reduce noise or improve sensitivity. Loop 19 is such an embodiment that uses multiple images taken over a time periods.

Turning now to FIG. 1, we see several embodiments or timing options of the UV light and the white light with respect to the animal's 24-hour period of nighttime and daytime. The white light is nominally off during the animal's night time, as shown, and on during the animal's daytime. Time a is the start of the animal's night. Time b is when night changes to day for the animal. Time i is the end of the animal's day. Typically time i is the time a for the next day.

The camera-visible white light must be turned off in order for the camera to properly see or ideally see the emission light from the fluorescence. It is undesirable to disturb or stress the animal by turning its perceived daylight off and on during its daytime. The UV light is within the normal spectral response of the animal but not within the normal spectral response of the camera. A camera filter (in the optical path of the camera) or source filter (in the path of the UV light) may be used to improve this performance.

The UV light may be left on all day. The white light may be left off all day, however, it is typically desirable to observe animal behavior using during its day, even though the animal may be nocturnal and less active during its day. Also, the cage may be equipped with an infrared (IR) light source and the camera may be sensitive to IR light. Such a configuration enables the camera to see during the animal's night and also during the animal's day, even with the white light off.

In one embodiment the white light is turned off at or approximately at the same time the UV light is turned on. If the animal's perception of light is approximately equally strong for the UV light and the visible light, such an embodiment provides perceived constant daylight for the animal. We see this simultaneous switching of the two light sources at times e and f in the Figure.

The UV light may be turned on prior to the white light being switched off, as we see at times c and d, respectively, in the Figure. The UV light may be left on after the white light is turned off, as shown at times h and g, respectively, in the Figure.

For convenience we show dot j, which may be when fluorescence is detected or first detected in the bedding. Such detection could potentially occur at any time during the animal's daytime when the UV light is on and the white light is off.

The lights may be pulsed, cycled regularly, cycled irregularly, or timed based on some other event. For example, if animal movement is detected or detectable, the UV light may be left off (or the white light left on) while the animal has not moved onto the bedding area and no fluorescence has been detected in the bedding.

Embodiments are claimed where no images are recorded during the animal's daytime and there is no animal movement and there is no reason to suspect that a location in the bedding has become fluorescent such the last recording time.

Embodiments are claimed where no video is analyzed for fluorescent emission during the animal's daytime and there is no animal movement and there is no reason to suspect that a location in the bedding has become fluorescent such the last analysis time.

Once fluorescent emission light is detected in the bedding, it may not be necessary to continue the UV light on; or may not be necessary to continue image recording; or may not be necessary to continue image analysis to locate emission light; or any combination.

Image analysis may occur after image recording. For example, although fluorescence was recorded at time j in the Figure, it was not detected through analysis until time g or h in the Figure.

Figure 2:
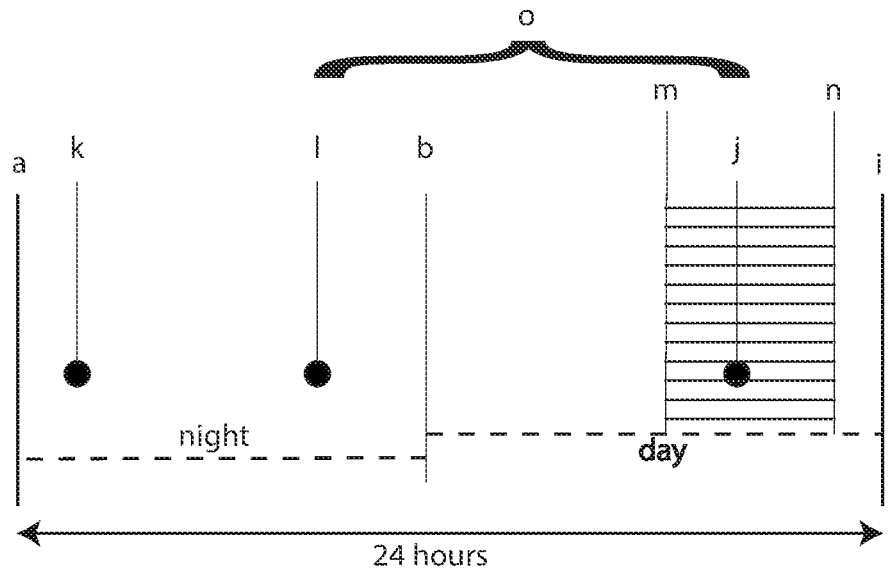
FIG. 2 shows a time-line for illumination in an animal cage.

Turning now to FIG. 2, we see a method of determining a time or time range for the feeding of the second food. The Figure shows the animal's night and daytimes, from time location a to b and b to i, respectively, as in FIG. 1. Embodiments may feed the second food at the start of the animal's day, not shown in the Figure.

Although prior art feeding of the second food traditionally occurs at the animal's morning, it may be advantageous for the second feeding to occur at a different time. The method comprises first determining an expected gut transit time, then adding time tolerance before and after to create a time window. Times m to n in the Figure show such a time window. Where the expected gut transit time is from l to j, as shown by o, in the Figure. It is then necessary to place this entire time window m to n within the daylight time of the animal, between b to i. From this, a range of possible second food feedings is computed. One such selected time is time l. Note that time k is not acceptable because time l to m would not place the entire time window m to n within the animal's daylight. Note also that the second feeding could not occur after b, because then time l to n would be after the end of the animal's day.

In this Figure, time j is both an expected gut transit time and a detected gut transit time, although these two times may be different.

Notes on Claims

The following comments on claims may be used, if necessary to maintain validity of a claim or to construe the claim. However, the following comments otherwise are exemplary embodiments only that in no way restrict the breadth of a claim.

A first time period may be used to assure an animal is hungry prior to the second time period so that it is likely that the animal will eat the second food. Time periods may a time interval, such as 3 hours, or may be a specific time, such as 8:00 am. In step (a), controlling the quantity of a first food at a first time period, that quantity may be zero for a non-zero first time period—in essence fasting the animal during this time period. The first time period may be zero—in essence feeding the second food immediately after the first food. If both the quantity of the first food is zero and the first time period is zero, in essence step (a) is nil or moot, which is specifically a claimed alternative embodiment. However, for the original claim as written, step (a) may not be nil, as then this limitation would effectively not exist.

The second time period, in step (b), may be a time window. For example, a second food may be presented to the animal at the start of a time window. Then, after some time following presentation, the animal eats the second food. When the animal actually eats the food, step (c) is executed—effectively starting the gut transit time clock when the animal eats the second food, rather than when the second food is offered.

In an alternate embodiment, the second time period is a time window, however, the gut transit time clock is started when the food is offered, not when it is actually eaten. For example, if a resolution of 30 minutes is desired for the final gut transit time measurement, a second time period window of 15 minutes may be adequate or appropriate. The second food may be withdrawn after this time window if the animal did not eat the second food.

Food may be solid, water or other liquid. Food may be the animal's regular food or special food. Feeding may include oral gavage.

Fluorescent includes phosphorescence.

The spectral band of ultra-violet (UV) light is the normal meaning of the term in the art. This band does not exclude light that might possibly be seen by a human eye. The band refers to light that is predominantly below the lower end of average human vision. It is, in the context of exciting fluorescent, "excitation light frequency band" means sufficiently overlapping the excitation band of the fluorescent material to excite it. Reference in literature that happens to list exact frequency bounds or an exact center frequency are not appropriate for construction. In addition, proper construction does not make UV light, "visible light," in the common usage of the word.

In step (d), "turning on" specifically includes "leaving on." A change of state of the light is not necessarily required. The UV light may be left on during all or a portion of the animal's daylight time period. It may be cycled or pulsed, either regularly or irregularly. The UV light may turned only when the animal is not blocking bedding that is desired to view with the camera. The UV light may turned on only when the animal is sleeping.

In step (e), "visible light" has two possible constructions for two different embodiments. First, visible light refers to nominally white light as perceived by a human. In this embodiment construction, it does not mean light that is exclusively visible to an animal. For a second embodiment, it means a light spectrum that predominantly overlaps (integration of total amplitude in the spectrum of greater than 50%) the sensitive range of a "visible light" camera (as distinct from an "infrared camera," for example). The camera may be a still, video, 3D or VR camera. It may be monochrome or color.

In step (f), a set of recorded images may be continuous, continual, or burst. Various image processing steps may be performed, such as frame deletion, frame decimation, pixel decimation, averaging, edge detection, cropping, masking, artifact removal, distortion correction (both chromatic and special), error detection, error correction, encryption, transmission, tagging, data overlays, watermarking, and the like. In particular, only areas of interest, such as portions of bedding, may be left in recorded images. Such optional image processing steps may be performed anywhere and at any appropriate time, such as in the camera, in an image-processing element prior to storage, during recording in non-transitory memory, or after a first, non-final, recording.

Bedding or bedding material in step (f) is also called litter. It may be any portion of the animal's cage or any material in the cage that collects some or all of animal excrement, included feces, droppings, urine saliva, blood, semen, skin, teeth, toenails, and the like. Although gut transit time generally refers to excrement, other embodiments and other modalities of animal excrement are claimed, in particular of the purpose of measuring or predicting disease progress; determining the appropriateness of any treatment or starting or terminating treatment; measuring the efficacy or side effects of treatment; predicting mortality; determining or validating disease models; and quantifying animal genotype. For example, hair loss may be related to cancer or cancer treatment, animal cleaning, compulsive behavior, or fighting. Blood loss may be due to disease, poor blood coagulation, poisoning, or infection with parasites.

In some embodiments, desired excrement passes through the bottom of the animal's nominal cage, and it is then in that final location that steps (f) and (g) are performed. One may extend the construction of "cage" to include such a space below the animal's restricted movement volume; and "bedding" to include that final collection area or material.

Some fluorescent materials may be chosen specifically for their vascular permeability or their lack of vascular permeability.

Embodiments include detecting fluorescence of born animals from the treated animal in steps (a) and (b).

Although prior art normally uses a single animal in a cage for measuring gut transit time, an embodiment is specifically claimed for multi-housed (also called multi-homed) animals where gut transit time is measured for all animals without regard to animal ID, such as the first animal's gut transit time or an average of the multiple animals' gut transit times. An embodiment is specifically claimed for multi-housed animals where gut transit time is measured for individual animals where gut transit time is identified for specific animals in the cage by determining automatically animal ID. Note that for this latter embodiment, animal ID is not necessary at step (b), if all animals consume the second food within the second time period. Multi-housed animals for gut-transit time measurements are novel and beneficial, for the afore-cited reasons.

Recording times in steps (c) and (h) may occur at any time, including before, during or after a preliminary time. For example, the second time period in (b) may be planed in advance. In step (h), multiple times may be predicted, and then invalid times later deleted. Processing steps may occur later or considerably later than steps involving the physical animal. For example, recorded video may be analyzed much later, subject to latter-determined requirements.

Embodiments include using different fluorescent dyes in the same cage; such as different excitation frequencies, different emission frequencies, or both. Different excitation light sources, different excitation light filters, different camera filters, or different colors of emission light may be used to differentiate multiple fluorescent dyes.

"Camera comprises a light filter" means that the light filter is anywhere in the optical path from the bedding to the camera light sensor.

"Passes" and "blocks" one or more light frequency bands means passing and attenuating light respectively so as to enable the embodiment to perform as intended. It is understood that light frequency bands of both sources and filters are not exact, in that they do not have "brick wall" cutoffs at frequencies, and that "passes" actually passes less than 100% and that "blocks" actually passes more than 0%.

"Light in the sensitive range of rodent eyes" may be approximately 395 nm, plus or minus a frequency range approximately equal to the width of the spectrum of the light, or equal to or approximately equal to half the width of the spectrum of the light. An embodiment is specifically claimed where the word, "rodent," is replaced with the word, "mouse."

In one embodiment, "visible light source" in step (e) means a light source that provides light in a daylight sensitive range of the eyes of a rodent or a mouse.

In one embodiment, "visible light source" in step (e) means a light source that provides light in a daylight sensitive range of an average human.

In one embodiment, "visible light source" in step (e) means a light source that provides light in a compatible spectrum as the camera.

"Human-visible-light-sensitive camera" means a camera designed to or adapted to respond to light compatible with the spectral response of normal human eyes. This may be a monochrome camera. The camera, whether monochrome or color, does not necessarily need to respond consistently to color or spectrum sensitivity of human eyes. It may also be sensitive to infrared (IR), for example. It may or may not have an IR filter, which may be fixed or mechanically adjustable to be in or out of the optical path.

"Light filter is adapted to be automatically, mechanically moved" means that a mechanism to move the filter may be controlled electrically or electronically, rather than manually at the location of the filter.

An "expected gut transit time" may be in the range of 1 to 36 hours, the range of 3 to 14 hours, the range of 4 to 12 hours, the range of 4 to 8 hours, or 6 hours. A gut transit time tolerance may be in the range of 1 to 12 hours, 2 to 6 hours, 3 to 6 hours, 2 to 4 hours, or 1 to 2 hours. They gut transit time tolerances may be asymmetric, that is, a first time may be subtracted from the expected gut transit time and a second time added to the expected gut transit time to create a detection time window. Expected gut transit time may be an average gut transit time for animals similar to the animal in a claim, with or without a range time tolerance.

The purpose of a claim directed to "selecting a detection time window" is so that step (d), turning on the UV light, occurs in the daylight for the animal. Some UV light frequencies are in the visible band of rodents. Thus, the UV light appears as visible light to the animal. It is undesirable to turn such rodent-visible light during the nighttime of the animal.

Embodiments are specifically claimed where the "feeding" in step (b) is replaced by "oral gavage," and also embodiments wherein step (a) is missing or optional.

Embodiments are specifically claimed where step (b) is replaced by:
"injecting the animal with a substance at a second time;
wherein the substance comprises a fluorescent dye;
wherein the fluorescent dye is responsive to an excitation light
frequency band and emits light in an emission light frequency band;" and wherein step (a) is optional.

Embodiments are specifically claimed where step (b) is replaced by:
"injecting the animal with a dose of fluorescent beads at a second time; wherein the fluorescent beads are responsive to an excitation light frequency band and emits light in an emission light frequency band;" and wherein step (a) is optional.

Embodiments are specifically claimed for claims directed to more than one animal in a cage, with changes consistent with steps (b) and (a) as described above.

Embodiments are specifically claimed where step (b) is replaced by:
"feeding the animal a dose of fluorescent beads at a second time;
wherein the fluorescent beads are responsive to an excitation light frequency band and emits light in an emission light frequency band;"

Embodiments are specifically claimed with the additional limitation:
"wherein the cage is a home cage of the animal, for steps (a) through (g)."

Embodiments are specifically claimed with the additional limitation:
"wherein the animal is not removed from its home cage, for steps (a) through (g)."

Embodiments are specifically claimed where the word "animal" in claims is replaced with the word "mouse."

Embodiments are specifically claimed where the word "animal" in claims is replaced with the word "rat."

Embodiments are specifically claimed where the word "animal" in claims is replaced with the word "rodent."

Embodiments are specifically claimed for devices and vivariums that implement the method of independent claim 13, as well as the methods of dependent claims and other embodiments of methods.

Methods of comparing to a disease model include but are not limited to: a LASSO analysis, a Fourier on a circle analysis; or an area-under-a-curve analysis. Methods also include curve fitting, regression analysis, RANSAC, Monte Carlo, simulated annealing and others known in the art maybe used to identify a relationship and fine-tune such a function that generates a distance or likelihood metric.

Selection of algorithms and adjusting coefficients may be accomplished by comparing application of such algorithms and coefficients to an existing gold standard or prior art results.

Bedding is any material that can receive excrement, described elsewhere herein. This is sometimes called litter. It may be simply a cage floor or grate. It may or may not be absorbent and may or may not pass urine.

A nexus of embodiments is that the UV light provides effective daylight for the animal, while turning off the white light enables the camera to see the emission light from the fluorescence.

A nexus of embodiments is that the camera in the claims is also used to observe the animal's activity in the cage using the white light.

A nexus of embodiments is that the camera in the claims is also used to observe the animal's activity in the cage using IR light during the nighttime period of the animal.

Embodiments are claimed wherein the camera is the only camera with a view of the cage bedding.

Embodiments are claimed wherein the cage comprises a red-light blocking filter.

Embodiments are claimed wherein the UV light source, the white light, and the camera share common electronics and are mounted proximally to each other.

Embodiments are claimed wherein the UV light source, the white light, and an IR light source share common electronics and are mounted proximally to each other.

Automated vivaria are more than simply taking prior art manual steps and automating them with known electronic equipment. Benefits of properly done automation, using the embodiments herein, provide (1) fewer errors; (2) more consistent results (e.g., smaller standard deviation); (3) more repeatable results (e.g., in time or in different vivaria); (4) lower cost; (5) better animal health; (6) better human technician health; (7) less danger of public exposure to pathogens; (8) higher detail of measurements, such as more frequent observations or higher precision of measurements; (9) detection of patterns not previously detectable, such as circadian rhythms; (10) measurement results free of animal stress due to handling or non-natural lighting, (11) detection of drug interactions or drug side effects not detectable with manual observations; (12) faster and more compressive studies leading to faster entry of human drugs into the market; and (13) identification of unexpected results in a study, such as may be detected only by a larger number of animal observations than feasible in the prior art.

Additional Embodiments

101. A method of measuring a gut transit time in an animal in a cage comprising the steps of:
   (a) controlling a quantity of the animal a first food at a first time period;
   (b) feeding the animal a second food at a second time period;
   wherein the second food comprises a fluorescent dye;
   wherein the fluorescent dye is responsive to an excitation light frequency band and emits light in an emission light frequency band;
   (c) recording the second time as a starting time;
   (d) turning on a ultraviolet (UV) light source in the cage; wherein the UV light source comprises light in the excitation light frequency band;
   (e) turning off a visible light source in the cage;
   (f) recording a set of recorded images, using a camera, of a bedding material in the cage during a first observation time interval;
   wherein the camera is responsive to light in the emission light frequency band;
   (g) detecting emission light of the dye in the bedding material in one or more detection images in the set of recorded images;
   (h) recording a time in which the one or more detection images were recorded, the ending time;
   (i) subtracting the starting time from the ending time, the result being the gut transit time;
   wherein step (b) occurs after step (a);
   wherein step (e) occurs after or at the same time as step (d).

102. The embodiment of embodiment 101 or claim 1 with the additional step:
   (o) recording video images of activity of the animal between steps (c) and (e);
   wherein the camera in step (f) is the same camera used in step (o).

103. The embodiment of embodiment 101 or claim 1 with the additional step:
   (p) recording video images of activity of the animal during a nocturnal time period of the animal;
   wherein the camera in step (f) is the same camera used in step (p).

104. The embodiment of embodiment 101 or claim 1:
   wherein the camera in step (f) is also sensitive to infrared (IR) light.

105. The embodiment of embodiment 101 or claim 1:
   wherein steps (a) through (g) are performed in a vivarium.

106. The embodiment of embodiment 101 or claim 1:
   wherein steps (a) through (g) are performed in a vivarium; and
   wherein the vivarium is lit by human-visible red light 107. The embodiment of embodiment 101 or claim 1:
   wherein steps (a) through (g) are performed in a vivarium; and
   wherein both the UV light source and the visible light source in steps (d) and (e) respectively are provided to each cage in a subset of cages in the vivarium separately.

108. The embodiment of embodiment 101 or claim 1:
   wherein steps (a) through (g) are performed in a vivarium;
   wherein the camera in step (f) is also sensitive to infrared (IR) light;
   wherein the cage comprises an IR light source;
   wherein steps (a) through (g) are performed in a vivarium;
   wherein all three of: the UV light source, the visible light source, and the IR light source are provided to each cage in a subset of cages in the vivarium separately.

Ideal, Ideally, Optimum and Preferred—Use of the words, "ideal," "ideally," "optimum," "optimum," "should" and "preferred," when used in the context of describing this invention, refer specifically a best mode for one or more embodiments for one or more applications of this invention. Such best modes are non-limiting, and may not be the best mode for all embodiments, applications, or implementation technologies, as one trained in the art will appreciate.

All examples are sample embodiments. In particular, the phrase "invention" should be interpreted under all conditions to mean, "an embodiment of this invention." Examples, scenarios, and drawings are non-limiting. The only limitations of this invention are in the claims.

May, Could, Option, Mode, Alternative and Feature—Use of the words, "may," "could," "option," "optional," "mode," "alternative," "typical," "ideal," and "feature," when used in the context of describing this invention, refer specifically to various embodiments of this invention. Described benefits refer only to those embodiments that provide that benefit. All descriptions herein are non-limiting, as one trained in the art appreciates.

All numerical ranges in the specification are non-limiting examples only.

Embodiments of this invention explicitly include all combinations and sub-combinations of all features, elements and limitation of all claims. Embodiments of this invention explicitly include all combinations and sub-combinations of all features, elements, examples, embodiments, tables, values, ranges, and drawings in the specification and drawings. Embodiments of this invention explicitly include devices and systems to implement any combination of all methods described in the claims, specification and drawings. Embodiments of the methods of invention explicitly include all combinations of dependent method claim steps, in any functional order. Embodiments of the methods of invention explicitly include, when referencing any device claim, a substation thereof to any and all other device claims, including all combinations of elements in device claims.

We claim:

1. A method of measuring a gut transit time in an animal in a cage comprising the steps of:
   (a) controlling a quantity of a first food for the animal at a first time period;
   (b) feeding the animal a second food at a second time period;
   wherein the second food comprises a fluorescent dye;
   wherein the fluorescent dye is responsive to an excitation light frequency band and emits light in an emission light frequency band;
   (c) recording the second time period as a starting time;
   (d) turning on a ultraviolet (UV) light source;
   wherein the UV light source comprises light in the excitation light frequency band;
   wherein the UV light source directs UV light to a bedding in the cage
   (e) turning off a human-visible light source;
   wherein the human-visible light source directs light to the bedding in the cage;
   (f) recording a set of photo images, using a camera, of the bedding material in the cage during a first observation time interval;
   wherein the camera is responsive to light in the emission light frequency band;
   (g) detecting emission light from the bedding in one or more detection images in the set of recorded photo images;
   (h) recording a time during which the one or more detection images were recorded, the ending time;
   (i) subtracting the starting time from the ending time, the result being the gut transit time;
   wherein step (b) occurs after step (a).

2. The method of measuring a gut transit time in claim 1:
   wherein the camera is a human-visible-light sensitive camera.

3. The method of measuring a gut transit time in claim 2:
   wherein a light filter is in the optical path of the camera;
   wherein the light filter passes light in the emission light frequency band and blocks light from the UV light source.

4. The method of measuring a gut transit time in claim 3:
   wherein the light filter is adapted to be automatically, mechanically moved into and out of the optical path from the bedding to an image sensor in the camera.

5. The method of measuring a gut transit time in claim 1:
   wherein the UV light comprises light in the sensitive range of rodent eyes.

6. The method of measuring a gut transit time in claim 1:
   wherein the cage houses one or more animals in addition to the animal.

7. The method of measuring a gut transit time in claim 6:
   wherein the food in step (b) is fed only to the animal, not to the one or animals in addition to the animal in the cage.

8. The method of measuring a gut transit time in claim 1 comprising the additional step:
   (j) selecting a detection time window consisting of an expected gut transit time plus-or-minus at least one gut transit time tolerance time interval;
   wherein the second time period is selected such that the entire detection time window, following the second time period, is within a daylight period of the animal.

9. The method of measuring a gut transit time in claim 1:
   (k) repeating steps (d) through (f) two or more times;
   wherein the "set of recorded photo images" in step (g) is any one or more of the sets of recorded photo images in steps (f).

10. The method of measuring a gut transit time in claim 9:
    wherein when the detecting step (g) so detects, step (k) terminates.

11. The method of measuring a gut transit time in claim 1:
    wherein the time in step (h) is the earliest time in which the one or more detection images were recorded.

12. The method of measuring a gut transit time in claim 1:
    wherein the feedings in steps (a) and (b) are controlled by an at least two-state device comprising the states: (i) the second food is not available; and (ii) the second food is available.

13. The method of measuring a gut transit time in claim 12:
    wherein the at least two-state device is automatic.

14. The method of measuring a gut transit time in claim 1:
    wherein step (a) occurs in the cage; and
    wherein the cage is a home-cage of the animal.

15. The method of measuring a gut transit time in claim 1:
    wherein step (a) occurs in the cage;
    wherein the cage is a home-cage of the animal;
    wherein the bedding in step (f) is a regular bedding of the home-cage of the animal; and
    wherein all steps are free of oral gavage of the animal.

16. The method of measuring a gut transit time in claim 1:
    wherein the time resolution of step (g) is five minutes or less.

17. The method of measuring a gut transit time in claim 1:
    wherein both a range of the UV light and a range of the visible light are restricted to the cage.

18. The method of measuring a gut transit time in claim 1 comprising the additional step:
    (l) recording a second set of photos, of a plurality of animal activities of the animal, in the cage, during a nighttime of the animal, using the camera, in infrared (IR) light;
    wherein step (l) occurs at any time from prior to step (a) to after step (i).

19. A method of determining a disease metric of an animal in a cage in a cage comprising the steps of:
   (m) repeating the method of claim 1 sequentially for two or more days;
   (n) aggregating the gut transit times of the repeating into a sequence;
   (o) comparing the sequence statistically to a first disease model;
   wherein the comparing generates a likelihood metric;
   wherein the likelihood metric is the disease metric.

20. A device that implements the method of claim 1.

21. A vivarium that implements the method of claim 1.

* * * * *